United States Patent [19]

Martin

[11] Patent Number: 4,812,580
[45] Date of Patent: Mar. 14, 1989

[54] PROCESS FOR THE PREPARATION OF 4-PHENYLPYRROLE DERIVATIVES

[75] Inventor: Pierre Martin, Rheinfelden, Switzerland

[73] Assignee: Ciba-Geigy Corporation, Ardsley, N.Y.

[21] Appl. No.: 93,449

[22] Filed: Sep. 4, 1987

Related U.S. Application Data

[62] Division of Ser. No. 773,706, Sep. 9, 1985, Pat. No. 4,709,053.

[30] Foreign Application Priority Data

Sep. 12, 1984 [CH] Switzerland ................. 4355/84

[51] Int. Cl.$^4$ .............................................. C07D 207/335
[52] U.S. Cl. ................................. 548/561; 548/530; 548/531
[58] Field of Search .................... 548/561, 530, 531

[56] References Cited

U.S. PATENT DOCUMENTS

| | | | |
|---|---|---|---|
| 3,775,477 | 11/1973 | Diana | 260/558 A |
| 4,471,126 | 9/1984 | Ueda et al. | 548/561 |
| 4,594,429 | 6/1986 | Ueda et al. | 548/530 |
| 4,680,413 | 7/1987 | Genda et al. | 548/561 X |
| 4,705,801 | 11/1987 | Martin et al. | 514/423 |

FOREIGN PATENT DOCUMENTS

| | | | |
|---|---|---|---|
| 0018473 | 11/1980 | European Pat. Off. | |
| 0111452 | 6/1984 | European Pat. Off. | |
| 1545831 | 7/1965 | Fed. Rep. of Germany | |
| 2927480 | 1/1980 | Fed. Rep. of Germany | |
| 1104323 | 2/1968 | United Kingdom | 548/531 |
| 1125169 | 8/1968 | United Kingdom | 548/531 |

OTHER PUBLICATIONS

Tetrahedron Letters No. 52, pp. 5337-5340 (1972), Van Leusen et al.
John M. Patterson; Recent Synthetic Methods for Pyrroles & Pyrrolenines, pp. 281-304 (1976).
Cheng et al., Synthesis of Substituted Porphyrins, pp. 1469-1472 (1977).
Chemical Abstracts, vol. 78, Jan.-Jun. 1973; Van Leusen et al: 111044x.
John D. Roberts, et al., Basic Principles of Organic Chemistry, pp. 320-321 (date unknown).
Noller, "Chemistry of Organic Compounds", 3rd ed, (1965), pp. 258-259; W. B. Saunders Co., Philadelphia and London.

Primary Examiner—Joseph Paul Brust
Attorney, Agent, or Firm—Kevin T. Mansfield; Edward McC. Roberts

[57] ABSTRACT

The invention relates to a process for the preparation of 4-phenylpyrrole derivatives of the formula I

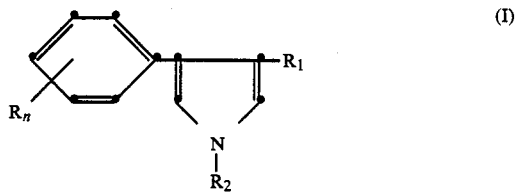

wherein $R_n$, $R_1$ and $R_2$ are as defined in claim 1, which comprises reacting a phenacylamine of formula II

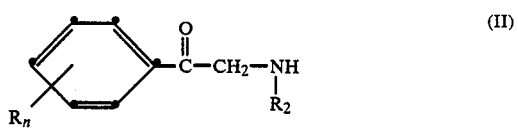

with a compound of formula III

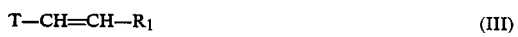

to give an intermediate of formula IV

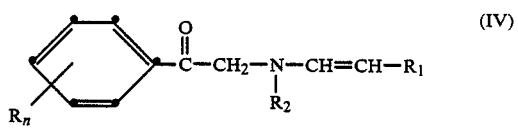

and cyclizing said intermediate, in the presence of a base, to give the compound I.

Important intermediates and novel final products are also described.

14 Claims, No Drawings

PROCESS FOR THE PREPARATION OF 4-PHENYLPYRROLE DERIVATIVES

This is a divisional of application Ser. No. 773,706 filed on Sept. 9, 1985 now U.S. Pat. No. 4,709,053, issued Nov. 24, 1987.

The present invention relates to a novel process for the preparation of 4-phenylpyrrole derivatives of the formula I

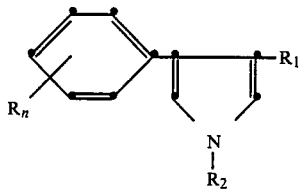

wherein $R_1$ is CN, CHO or $COO(C_1-C_6)$alkyl, $R_2$ is hydrogen, $CH_2CH_2CN$ or $CH_2CH_2COO(C_1-C_6)$alkyl, R is halogen, $C_1-C_6$alkyl or $C_1-C_6$haloalkyl, and n is 0, 1 or 2.

Depending on the indicated number of carbon atoms, alkyl by itself or as moiety of another substituent, such as haloalkyl and the like, comprises e.g. the following straight chain or branched groups: methyl, ethyl, propyl, butyl, pentyl, hexyl etc., and the isomers thereof, e.g. isopropyl, isobutyl, tert-butyl, isopentyl etc. Throughout this specification, a substituent prefixed by "halo" will be understood as meaning that said substituent may be monohalogenated or perhalogenated. Halogen and halo signify in particular fluorine, chlorine or bromine. Hence haloalkyl denotes a monohalogenated to perhalogenated alkyl radical, e.g. $CHCl_2$, $CH_2F$, $CCl_3$, $CH_2Cl$, $CHF_2$, $CH_2CH_2Br$, $C_2Cl_5$, $CHBr$, $CHBrCl$ etc., with $CF_3$ being preferred. 4-Phenylpyrrole derivatives of formula I, wherein n is 0, 1 or 2, $R_1$ is cyano and $R_2$ is hydrogen or acetyl, are known as plant fungicides from German Offenlegungsschrift 29 27 480[1]). As will be shown below, compounds of formula I, wherein $R_1$ is CHO or $COO(C_1-C_6)$alkyl or $R_2$ is $CH_2CH_2CN$ or $CH_2CH_2COO(C_1-C_6)$alkyl, can be converted in simple manner into the known fungicidal 4-phenyl-3-cyanopyrroles and thus have the character of intermediates.

A process for the preparation of 4-phenyl-3-cyanopyrrole derivatives which is known from Tetrahedron Letters No. 52, pp. 5337–5340, 1972[2]), is disclosed in German Offenlegungsschrift 29 27 480[1]). In this process, known as the TosMIC process, a cinnamic acid derivative of formula X

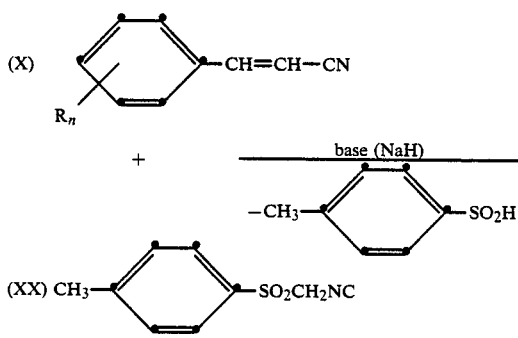

is cyclised with tosyl methyl isocyanide (XX) [TosMIC], in the presence of a strong base, e.g. sodium hydride, to give 4-phenyl-3-cyanopyrrole derivatives of formula (XXX). In the above formulae, R is as defined for formula I and n is 0, 1 or 2.

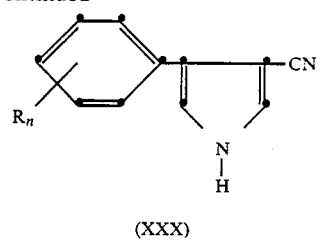

Although numerous pyrrole syntheses are known (q.v. J. M. Patterson, Synthesis 1976, pp. 281–304[3])), only the TosMIC process outlined above has so far led direct to the fungicidally useful 4-phenyl-3-cyanopyrrole derivatives. However, reference (2) indicates for the preparation of 4-phenyl-3-cyanopyrrole a yield of only 35%, which is low for industrial purposes. It has been found that the reagent TosMIC has grave disadvantages for industrial syntheses. For example, at elevated temperatures above 90° C. (normal drying conditions), TosMIC has the propensity to decompose explosively. On the other hand, residual moisture consumes some of the base employed (danger of hydrolysis/reduction in yield). Further, TosMIC has physiological hazards and causes severe irritation to the eyes and skin.

The shortcomings referred to above show that useful laboratory methods are unsuitable for the industrial production of 4-phenylpyrrole derivatives. A novel, more economic and environmentally more acceptable process for the preparation of these compounds in surprisingly high yield has now been found.

The novel process of this invention for the preparation of the 4-phenylpyrrole derivatives of the formula I as defined at the outset comprises reacting a phenacylamine of formula II

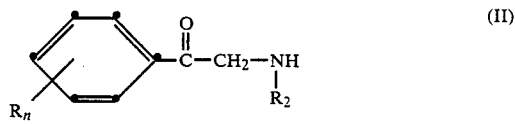

in the form of an acid addition salt, with a compound of formula III $$T-CH=CH-R_1 \quad (III)$$

to give an intermediate of formula IV

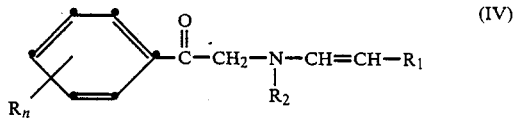

and cyclising this compound of formula IV, in the presence of a base, to a compound of formula I. In the formulae II, III and IV above, the substituents $R_1$, $R_2$ and $R_n$ are as defined for formula I, T is a group selected from $-OZ$, $-N(R_3)(R_4)$, $-OCOR_a$, $-OSO_2R_b$, $-SR_c$ or halogen, where Z is $C_1-C_6$alkyl, unsubstituted or substituted phenyl, an alkali metal atom or an alkaline earth metal atom, each of $R_a$ and $R_b$ independently of the other is $C_1$-$C_6$alkyl or unsubstituted or substituted phenyl, $R_c$ is $C_1$-$C_3$alkyl, $C_1$-$C_3$haloalkyl or unsubstituted or substituted phenyl; and each of $R_3$ and $R_4$ independently of the other is $C_1$-$C_6$alkyl or, together with the amine nitrogen atom, form a saturated 5- or 6-membered heterocyclic ring which contains, as hetero atom, either only the amine nitrogen atom or a further hetero atom.

An unsubstituted or substituted phenyl group is in particular phenyl or phenyl whichis substituted in the para-position by halogen, preferably chlorine or bromine, and by $C_1$-$C_3$alkyl, preferably methyl. Alkali metal atoms or alkaline earth meta l atoms may be Li, Na and K, preferably Na and K, or Mg, Ca, Sr and Ba, preferably Mg, Ca and Ba. Where the —N($R_3$)($R_4$) group denotes a saturated 5- or 6-membered heterocyclic ring containing N as hetero atom or a further hetero atom, said ring may be selected from the following heterocyclic ring systems: pyrrolidine, piperazine, perhydrothiazine, morpholine, piperazine, oxazolidine, thiazolidine, imidazolidine, pyrazoline and the like. A further hetero atom is preferably N, O or S.

In the process of this invention it is not necessary to isolate the intermediate (IV) first and then to cyclise it to compounds of formula I. To the contrary, the reaction of (II) with (III) may also be carried out direct in the presence of a base, utilising a single reaction vessel for both steps, to give the final products. In this procedure, the intermediate (IV) is further processed direct without isolation. On the other hand, it may be convenient to prepare the intermediate (IV) first in especially pure form, e.g. by repeated recrystallisation, and then to cyclise it to a compound of formula I. A preferred embodiment of the process of this invention accordingly comprises reacting the phenacylamine II in the form of an acid addition salt, in the presence of a base, direct with a compound of formula III to give the final product I.

The second preferred embodiment of the process conprises first reacting the phenacylamine II in the form of an acid addition salt, in the absence of a base, to give the intermediate (IV) and then converting (IV) to (I) by cyclisation in the presence of a base.

The reactants (II), (III) and, where appropriate, (IV), are conveniently employed in equimolar amounts. It is preferred to add an equimolar amount or an excess of base.

Typical representatives of the compounds of formula III, the list of which is not exhaustive, are the following compounds (a) to (t), of which compounds (a) to (l) are particularly advantageous and therefore preferred:

$(CH_3)_2N-CH=CH-CN$ (a)
$(C_2H_5)_2N-CH=CH-CN$ (b)

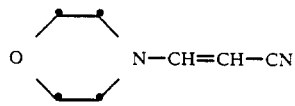 (c)

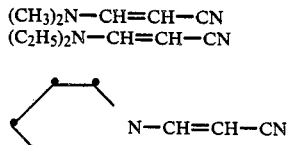 (d)

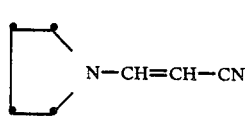 (e)

$NaO-CH=CH-CN$ (f)
$KO-CH=CH-CN$ (g)
$(CH_3)_2N-CH=CH-COOCH_3$ (h)
$(C_2H_5)_2N-CH=CH-COOCH_3$ (i)
$(CH_3)_2N-CH=CH-CHO$ (k)
$(C_2H_5)_2N-CH=CH-CHO$ (l)
$Cl-CH=CH-CN$ (m)
$Cl-CH=CH-COOCH_3$ (n)
$CH_3O_2SO-CH=CH-CN$ (o)
$[C_6H_4CH_3(4)]-CH=CH-CN$ (p)
$CH_3O-CH=CH-CN$ (q)
$C_2H_5O-CH=CH-CN$ (r)
$C_3H_7O-CH=CH-CN$ (s)
$[C_6H_4Cl(4)]O-CH=CH-COOCH_3$ (t)

The process of this invention is conveniently carried out in an inert solvent or mixture of solvents. Thus one or more inert solvents or diluents may be employed. Examples of suitable solvents and diluents are: aliphatic and aromatic hydrocarbons such as benzene, toluene, xylenes, petroleum ether; halogenated hydrocarbons such as chlorobenzene, methylene chloride, ethylene chloride, chloroform, carbon tetrachloride, tetrachloroethylene; ethers and ethereal compounds such as dialkyl ethers (diethyl ether, diisopropyl ether, tert-butylmethyl ether etc.), anisole, dioxane, tetrahydrofuran; nitriles such as acetonitrile and propionitrile; N,N-dialkylated amides such as dimethylformamide; dimethylsulfoxide; ketones such as acetone, diethyl ketone, methyl ethyl ketone; alcohols, in particular methanol, ethanol, propanols, butanols and the like; and water and aqueous two-phase mixtures and mixtures of the above solvents.

The following solvents for example are suitable for the organic water-immiscible phase: aliphatic and aromatic hydrocarbons such as pentane, xylenes etc.; halogenated hydrocarbons such as dichloromethane, chloroform, carbon tetrachloride, ethylene dichloride, 1,2-dichloroethane, tetrachloroethylene and the like, or aliphatic ethers such as diethyl ether, diisopropyl ether, tert-butylmethyl ether and the like. The addition of a phase transfer catalyst may be advantageous. Examples of suitable phase transfer catalysts are: tetraalkylammonium halides, hydrogen sulfates or hydroxides, e.g. tetrabutylammonium chloride, tetrabutylammonium bromide, tetrabutylammonium iodide, triethylbenzylammonium chloride or triethylbenzylammonium bromide, tetrapropylammonium chloride, tetrapropylammonium bromide or tetrapropylammonium iodide etc. Suitable phase transfer catalysts are also phosphonium salts. The ammonium salt of formula II itself acts as phase transfer catalyst.

Particularly suitable solvents are nitriles and lower alkanols, preferably acetonitrile and ethanol, as well as mixtures of alkanol/water (ethanol/water).

In all partial steps and in the single vessel reaction, the reaction temperatures are generally in the range from 0° to +120° C., preferably from +30° to +80° C.

Owing to the reduced thermal stability of the starting phenacylamine, the compound of formula II is emplyed inthe form of its more stable ammonium salt, which can be obtained by conventional addition of an organic or inorganic acid to the free amine.

Examples of salt-forming acids are inorganic acids, e.g. hydrohalic acids such as hydrofluoric acid, hydrochloric acid, hydrobromic acid or hydriodic acid, as well as sulfuric acid, phosphoric acid, phosphorous acid, nitric acid and the like; and organic acids such as acetic acid, trifluoroacetic acid, trichloroacetic acid, propionic acid, glycollic acid, lactic acid, succinic acid, benzoic acid, cinnamic acid, oxalic acid, formic acid, benzenesulfonic acid, p-toluenesulfonic acid, methanesulfonic acid, sallicyclic acid, 2-phenoxybenzoic acid or 2-acetoxybenzoic acid and the like.

Preferred salt-forming acids are strong acids such as the hydrohalic acids, phosphoric acid, nitric acid, and the sulfonic acids such as p-toluenesulfonic acid. Hydrochloric acid is especially preferred.

The reaction of (II) with (III) direct to give (I), or of (IV) to give (I), is conducted in the presence of a base. Examples of suitable bases are inorganic bases such as the oxides, hydrides, hydroxides, carbonates, carboxylic acid salts and alcoholates of alkaline earth metals, preferably of alkali metals, in particular of sodium and potassium [e.g. NaH, NaOH, KOH, $Na_2CO_3$, $K_2CO_3$, $CaCO_3$, $CH_3COONa$, $C_2H_5COOK$, $C_2H_5ONa$, $CH_3ONa$ and the like], preferably the alkali metal alcoholates such as sodium ethylate or sodium methylate. Suitable organic bases are e.g. triethylamine, piperidine, pyridine, 4-dimethylaminopyridine and the like.

In the processes of this invention, intermediates and final products may be isolated from the reaction mediu and, if desired, purified by one of the commonly employed methods, for example by extraction, crystallisation, chromatography, distillation and the like. However, the preparation of the compounds of formula I can be carried out generally in good yield and in excellent purity utilising a single vessel for both reaction steps without isolation of intermediates.

Preferred embodiments of the process of this invention are e.g. those which comprise:

(a) the use of starting materials of formula II, wherein R is halogen, preferably fluorine, chlorine or bromine, most preferably chlorine, n is 1 or preferably 2, with the proviso that, if n is 2, the ortho- and meta-positions are particularly preferred, $R_1$ is CN and $R_2$ is hydrogen;

(b) the use of reagents of formula III, wherein T is a group selected from —$N(CH_3)_2$, —$N(CH_2H_5)_2$,

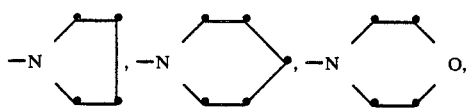

—OK or —ONa, and $R_1$ is CN, $COOCH_3$ or CHO, preferably CN;

(c) the use of intermediates of formula IV, wherein $R_1$, $R_2$ and $R_n$ are as defined in (a) and (b) above;

(d) the use of acid addition salts of formula II, which contain, as acid component, a hydrohalic acid, preferably hydrochloric acid, a sulfonic acid, preferably benesulfonic or p-toluenesulfonic acid, or sulfuric acid;

(e) carrying out the reaction of (II) with (III) such that the intermediate IV is further processed direct without isolation;

(f) carrying out the process in the temperature range from +30° to +80° C.

Accordingly, a particularly preferred embodiment of the process of the invention comprises reacting 2,3-dichlorophenacylamine in the form of an acid addition salt, preferably in the form of the hydrochloride, with a compound of formula III, wherein $R_1$ is CN and T is a group selected from —$N(CH_3)_2$,

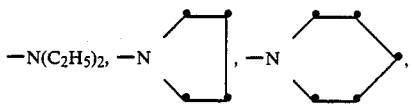

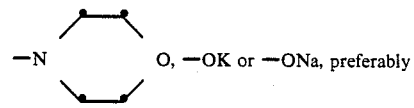

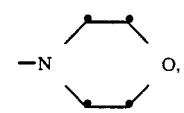

to give 3-(2,3-dichlorophenacylamino)acrylonitrile, and cyclising this intermediate, either as substance or preferably in situ, in the presence of a base, preferably of a lower alkanolate, sodium hydroxide, potassium hydroxide, sodium acetate, potassium acetate or a tri-lower alkylamine, to give 4-(2,3-dichlorophenyl)-3-cyanopyrrole.

Most of the starting materials of formula II are known or can be prepared in similar manner to the known representatives. However, 2,3-dichlorophenacylamine and the acid addition salts thereof are novel. In view of its structure, this compound is destined for use as intermediate for the preparation of fungicidally active 4-(2,3-dichlorophenyl)-3-cyanopyrrole and therefore constitutes an object of this invention. Its preparation will be described explicitly below.

Compounds of formula II, wherein $R_2$ is $CH_2CH_2CN$ or $CH_2CH_2COO(C_1-C_6)alkyl$, can be prepared e.g. as follows from the starting phenacylamines (II) ($R_2=H$): The acid addition salt (e.g. the HCl salt) of an N-substituted phenacylamine of formula II is reacted, in the presence of an equimolar amount of acrylonitrile or of a $C_1-C_6$alkyl ester of acrylic acid, preferably in the presence of one of the bases specified above and under the conditions for the reaction of (II), with (III) to give (I).

Within the scope of the present invention, typical representatives of compounds of formula I are for example the compounds listed in Table 1.

TABLE 1

Compounds of formula II (II)

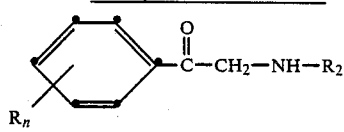

| Compound | $R_n$ | $R_2$ |
|---|---|---|
| 1.1 | H | H |
| 1.2 | 3-Cl | H |
| 1.3 | 2,4-$Cl_2$ | H |
| 1.4 | 4-Cl | H |
| 1.5 | 4-F | H |

TABLE 1-continued

Compounds of formula II $$\text{R}_n\text{-C}_6\text{H}_{4-n}\text{-C(=O)-CH}_2\text{-NH-R}_2 \quad (II)$$

| Compound | $R_n$ | $R_2$ |
|---|---|---|
| 1.6 | 3-CH$_3$ | H |
| 1.7 | 3-F | H |
| 1.8 | 3-Br | H |
| 1.9 | 3-CF$_3$ | H |
| 1.10 | 2-Cl | H |
| 1.11 | 2,3-Cl$_2$ | H |
| 1.12 | 2,5-Cl$_2$ | H |
| 1.13 | 2-Br | H |
| 1.14 | 2,6-Cl$_2$ | H |
| 1.15 | H | CH$_2$CH$_2$CN |
| 1.16 | 3-Cl | CH$_2$CH$_2$CN |
| 1.17 | 2-Cl | CH$_2$CH$_2$CN |
| 1.18 | 2,3-Cl$_2$ | CH$_2$CH$_2$CN |
| 1.19 | 3-F | CH$_2$CH$_2$CN |
| 1.20 | 3-Cl | CH$_2$CH$_2$COOCH$_3$ |
| 1.21 | 2,3-Cl$_2$ | CH$_2$CH$_2$COOCH$_3$ |
| 1.22 | 2-Cl | CH$_2$CH$_2$COOCH$_3$ |
| 1.23 | 2,3-Cl$_2$ | CH$_2$CH$_2$COOC$_2$H$_5$ |
| 1.24 | 2,3-Cl$_2$ | CH$_2$CH$_2$COOC$_3$H$_7$ |
| 1.25 | 2-Br | CH$_2$CH$_2$COOCH$_3$ |

The compounds of formula III are in general commercially available and thus known substances or compounds which can be prepared in similar manner to their known representatives.

The preparation of the intermediates of formula IV is an object of the present invention and has been described in detail above. These intermediates IV can be converted by simple basic cyclisation into the useful fungicides of formula I, have themselves fungicidal activity, and accordingly constitute an essential object of the present invention.

Within the scope of this invention, typical representatives of intermediates of formula IV are:

TABLE 2

Compounds of the formula $$\text{R}_n\text{-C}_6\text{H}_{4-n}\text{-C(=O)-CH}_2\text{-N(R}_2\text{)-CH=CH-R}_1 \quad (IV)$$

| Compound | $R_n$ | $R_2$ | $R_1$ |
|---|---|---|---|
| 2.1 | H | H | CN |
| 2.2 | 3-Cl | H | CN |
| 2.3 | 2,4-Cl | H | CN |
| 2.4 | 4-Cl | H | CN |
| 2.5 | 4-F | H | CN |
| 2.6 | 3-CH$_3$ | H | CN |
| 2.7 | 3-F | H | CN |
| 2.8 | 3-Br | H | CN |
| 2.9 | 3-CF$_3$ | H | CN |
| 2.10 | 2-Cl | H | CN |
| 2.11 | 2,3-Cl$_2$ | H | CN |
| 2.12 | 2,5-Cl$_2$ | H | CN |
| 2.13 | 2-Br | H | CN |
| 2.14 | 2,6-Cl$_2$ | H | CN |
| 2.15 | 2,3-Cl$_2$ | H | COOCH$_3$ |
| 2.16 | H | H | CHO |
| 2.17 | 3-Cl | H | COOCH$_3$ |
| 2.18 | 3,4-Cl$_2$ | H | COOCH$_3$ |
| 2.19 | 2-Cl | H | COOCH$_3$ |
| 2.20 | 2,3-Cl$_2$ | H | COOCH$_3$ |
| 2.21 | 2,3-Cl$_2$ | CH$_2$CH$_2$COOCH$_3$ | CN |
| 2.22 | 2,3-Cl$_2$ | CH$_2$CH$_2$CN | CN |
| 2.23 | H | CH$_2$CH$_2$CN | CN |
| 2.24 | 3-Cl | CH$_2$CH$_2$CN | CN |
| 2.25 | 2-Cl | CH$_2$CH$_2$CN | CN |
| 2.26 | 2,3-Cl$_2$ | CH$_2$CH$_2$COOC$_2$H$_5$ | CN |
| 2.27 | 3-F | CH$_2$CH$_2$CN | CN |
| 2.28 | 3-Cl | CH$_2$CH$_2$COOCH$_3$ | CN |
| 2.29 | 2-Cl | CH$_2$CH$_2$COOCH$_3$ | CN |
| 2.30 | 2,3-Cl$_2$ | CH$_2$CH$_2$COOC$_3$H$_7$ | CN |
| 2.31 | 2-Br | CH$_2$CH$_2$COOCH$_3$ | CN |
| 2.32 | 2,3-Cl$_2$ | CH$_2$CH$_2$CN | CHO |

As mentioned at the outset, some of the compounds of formula I have the character of intermediates. These compounds are the representatives of formula I hereinafter referred to as subgroup Ia, wherein $R_n$ is as defined for formula I; and in those compounds in which $R_1$ is CHO or COO(C$_1$-C$_6$)alkyl, $R_2$ is at the same time hydrogen, CH$_2$CH$_2$CN or CH$_2$CH$_2$COO(C$_1$-C$_6$)alkyl, or in those compounds in which $R_1$ is CN, $R_2$ is at the same time CH$_2$CH$_2$CN or CH$_2$CH$_2$COO(C$_1$-C$_6$)alkyl. These novel pyrrole derivatives, which also have fungicidal properties, can be converted in simple manner into the fungicidal 4-phenyl-3-cyanopyrroles known from German Offenlegungsschrift 29 27 480, as CHO and COO(C$_1$-C$_6$)alkyl can be converted into CN, and CH$_2$CH$_2$CN and CH$_2$CH$_2$COO(C$_1$-C$_6$)alkyl as substituents at the pyrrole nitrogen atom are easily removable groups. On account of these advantageous properties, the compounds of subgroup Ia constitute a further object of the present invention.

Typical examples of compounds of subgroup Ia are listed below.

TABLE 3

Compounds of formula Ia $$\text{(Ia)}$$

| Compound | $R_n$ | $R_1$ | $R_2$ |
|---|---|---|---|
| 3.1 | H | CHO | H |
| 3.2 | 3-Cl | CHO | H |
| 3.3 | 2,4-Cl$_2$ | CHO | H |
| 3.4 | 4-Cl | CHO | H |
| 3.5 | 4-F | CHO | H |
| 3.6 | 3-CH$_3$ | CHO | H |
| 3.7 | 3-F | CHO | H |
| 3.8 | 3-CF$_3$ | CHO | H |
| 3.9 | 2,3-Cl$_2$ | CHO | H |
| 3.10 | 2,6-Cl$_2$ | CHO | H |
| 3.12 | 3-Cl | COOCH$_3$ | H |
| 3.13 | 2-Cl | COOCH$_3$ | H |
| 3.14 | 4-F | COOCH$_3$ | H |
| 3.15 | 2,3-Cl$_2$ | COOCH$_3$ | H |
| 3.16 | 3-Cl | CN | CH$_2$CH$_2$CN |
| 3.17 | 2-Cl | CN | CH$_2$CH$_2$CN |
| 3.18 | 3-CH$_3$ | CN | CH$_2$CH$_2$CN |
| 3.19 | 2,3-Cl$_2$ | CN | CH$_2$CH$_2$CN |
| 3.20 | 4-F | CN | CH$_2$CH$_2$COOCH$_3$ |
| 3.21 | 2-Cl | CN | CH$_2$CH$_2$COOCH$_3$ |
| 3.22 | 2,3-Cl$_2$ | CN | CH$_2$CH$_2$COOCH$_3$ |

TABLE 3-continued

Compounds of formula Ia (Ia)

| Compound | $R_n$ | $R_1$ | $R_2$ |
|---|---|---|---|
| 3.23 | 2,3-$Cl_2$ | CHO | $CH_2CH_2COOCH_3$ |
| 3.24 | 2,3-$Cl_2$ | $COOCH_3$ | $CH_2CH_2CN$ |

The conversion of CHO into CN can be effected in a manner known per se, for example as follows: An aldehyde of formula I ($R_1$=CHO) is converted at 0° to 100° C., in an inert solvent (e.g. an alcohol, an ether, pyridine, triethylamine and the like) into the corresponding oxime (syn/anti mixture), which is converted into the nitrile by treatment with a dehydrating agent (e.g. acetic anhydride, cyanuric chloride/pyridine, $(PNCl_2)_3$, dicyclohexyldicarbodiimide/$CuCl_2$/triethylamine, $P_2O_5$, tosyl chloride/pyridine, $TiCl_4$/pyridine and the like).

If it is desired to convert the ester group $COO(C_1$-$C_6)$alkyl into the CN group, a start is best made from the free acid, which is prepared in a manner known per se by ester hydrolysis with an aqueous mineral acid (e.g. HCl/$H_2O$), in the presence of a solubiliser (e.g. alcohol, dioxane, tetrahydrofuran and the like), most conveniently under reflux temperature. The free acid is then converted into the acid amide either direct with ammonia at elevated temperature or via the acid chloride (—COOH+thionyl chloride→COCl) with ammonia at room temperature, and the acid amide is converted to the nitrile with one of the previously mentioned dehydrating agents in the temperature range from 80° to 220° C.

If it is desired to form the free pyrrole by removal of the $CH_2CH_2CN$ or $CH_2CH_2COO(C_1$-$C_6)$alkyl radical, this may be done e.g. by treatment with a base in the temperature range from −20° to +180° C., in a suitable inert solvent. Exemplary of suitable reaction conditions are:

(a) sodium hydride in dimethylformamide at 0° C.
(b) ammonia/water/dioxane at 180° C.
(c) potassium hydroxide/water/alcohol at 100° C.

PREPARATORY EXAMPLES

Example P1

Preparation of

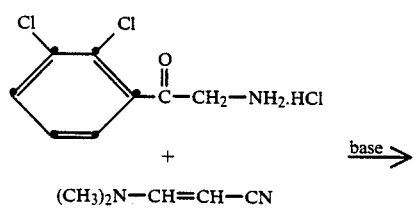

+ $(CH_3)_2N$—CH=CH—CN $\xrightarrow{base}$

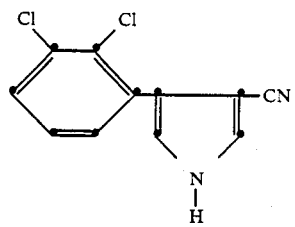

4-(2,3-Dichlorphenyl)-3-cyanopyrrole (a) Preparation of the precursor: N-acetyl-2,3-dichlorophenacylamine 150 g of 2,3-dichlorobenzoyl cyanide are hydrogenated with elemental hydrogen under normal pressure at 70° C. in 1.5 l of glacial acetic acid and 84.15 g of acetic anhydride over 5 g of $PtO_2$. After absorption of 112% of the calculated amount of hydrogen (time taken: c. 5 hours), the hydrogenation is discontinued, the reaction mixture is filtered and the filtrae is concentrated by evaporation. The residual yellow oil is crystallised by addition of hexane/diethyl ether. The crystalline product is isolated by filtration and dried. M.p. 107°–109° C. IR (solid/KBr) in cm$^{-1}$: 3300 (NH); 1735 (CO); 1650 (CO). $^1$H-NMR ($CDCl_3$) in ppm: 2.08 (s, 3H); 4.55 (d, 2H); 6.2–6.6 (broad s, 1H); 7.25 (m, 3H).

(b) Preparation of the precursor: 2,3-dichlorophenacylamine hydrochloride 50.0 g of the N-acetyl-2,3-dichlorophenacylamine obtained in (a) are heated for 2 hours under reflux in 500 ml of hydrochloric acid. The slightly turbid reaction solution is concentrated by evaporation and the residue is digested with ethyl acetate. The crystalline 2,3-dichlorophenacylamine hydrochloride is isolated by filtration and dried. Melting point: 217°–218° C. IR (solid/KBr) in cm$^{-1}$: 1695 (CO). (Another crystal modification shows two carbonyl resonance bands at 1690 and 1705 cm$^{-1}$). $^1$H-NMR (DMSO, d6) in ppm: 4.54 (s, 2H); 7.6 (t, 1H); 7.9 (m, 2H); 8.6 (s, 3H, replaceable with $D_2O$).

(c) Preparation of the final product: 4-(2,3-dichlorophenyl)-3-cyanopyrrole 20.0 g of 2,3-dichlorophenacylamine hydrochloride and 10.0 g of 3-dimethylaminoacrylonitrile are heated for 1 hour under reflux in 300 ml of ethanol. Then an ethanolic solution of sodium ethylate, prepared from 2.1 g of sodium and 30 ml of ethanol, is rapidly added dropwise and the reaction mixture is stirred for another 10 minutes under reflux. The reaction mixture is cooled to room temperature and then poured into ice/hydrochloric acid and the resultant mixture is stirred for 1½ hours. The precipitate is isolated by filtration, washed with water and dried, affording 15.4 g (78% of theory) of title compound with a melting point of 152°–154° C.

Examples P2 to P4

Preparation of

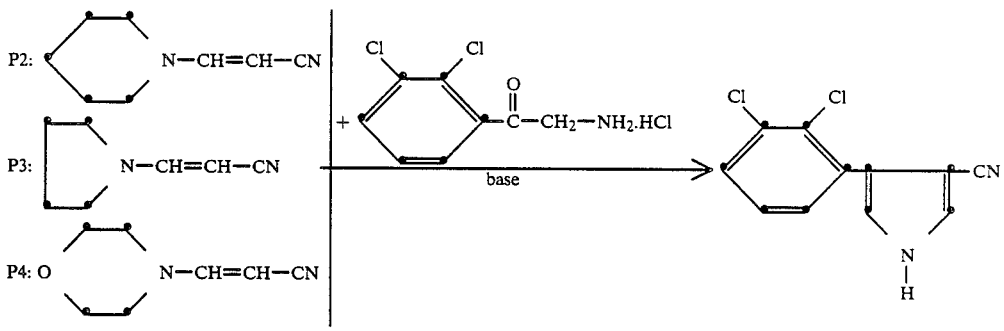

4-(2,3-Dichlorophenyl)-3-cyanopyrrole

Following the procedure described in Example P1c), but replacing 3-dimethylaminoacrylonitrile by
N-piperidinylacrylonitrile,
N-pyrrolidinylacrylonitrile, or
N-morpholinylacrylonitrile,
and increasing the reaction time from 1 hour to 3 to 4 hours, pure 4-(2,3-dichlorophenyl)-3-cyanopyrrole is obtained in all three Examples in yields ranging from 76 to 85% of theory. Melting point: 150°–154° C.

Example P5

Preparation of

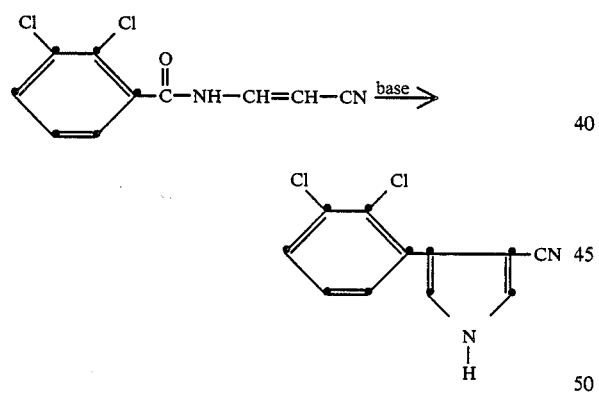

4-(2,3-dichlorophenyl)-3-cyanopyrrole (a) Preparation of the intermediate:
3-(2,3-dichlorophenacylamino)acrylonitrile 20.0 g of 2,3-dichlorophenacylamine hydrochloride and 10.0 g of 3-dimethylaminoacrylonitrile are heated for 1 hour under reflux in 300 ml of ethanol. After cooling it to room temperature, the reaction solution is poured into a mixture of ice/dilute hydrochloric acid. After extraction with ethyl acetate, the combined extracts are dried over sodium sulfate, filtered, and the filtrate is concentrated. The oily residue is purified by column chromatography (silica gel: elution with a 4:1 mixture of toluene/ethyl acetate). M.p. 125°–127° C. IR (solid/KBr) in cm$^{-1}$: 3380 (NH), 2200 (CN), 1715 (CO) 1625 (C=C). $^1$H-NMR (DMSO$_{d6}$) in ppm: 4.09 (d, J=15 Hz, 1H); 4.46 (d, J=7 Hz, 2H); 7.2 (q, 1H); 7.4 (broad s, 1H); 7.45–7.85 (m, 3H). Mass spectrum: molecular peak at 254.

(b) Preparation of the final product:
4-(2,3-dichlorophenyl)-3-cyanopyrrole

To 4.2 g of the 3-(2,3-dichlorophenacylamino)acrylonitrile obtained in (a) is added 0.5 g of sodium ethylate in 50 ml of ethanol. The reaction mixture is heated to reflux temperature, cooled to room temperature, poured into a mixture of dilute hydrochloric acid and ice, and stirred for c. 1 hour. The precipitate is isolated by filtraion, washed with water and dried, affording the title compound in quantitative yield. Melting point: 149°–150° C.

Example P6

(Formulae, see Ex. P5)

(a) Preparation of the intermediate:
3-(2,3-dichlorophenacylamino)acrylonitrile 2 g of 2,3-dichlorophenacylamine hydrochloride, 1 g of 3-hydroxyacrylonitrile, sodium salt, and 20 ml of ethanol are heated for 2 hours under reflux. The reaction mixture is concentrated by evaporation and the oily residue is purified by column chromatography (silica gel; elution with a 4:1 mixture of tolluene/ethyl acetate), affording 3-(2,3-dichlorophenacylamino)acrylonitrile in the cis/trans ratio of 5:1. Melting point: 122°–125° C.

(b) Preparation of the final product:
4-(2,3-dichlorophenyl)-3-cyanopyrrole 4.2 g of the 3-(2,3-dichlorophenacylamino)acrylonitrile obtained in (a) are reacted in 50 ml of ethanol with 0.5 g of sodium ethylate as described in Example P5 (b), affording the title compound in quantitative yield. Melting point: 150°–152° C.

Example P7

Preparation of

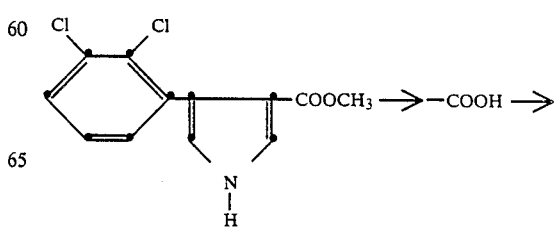

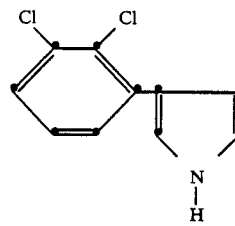

4-(2,3-dichlorophenyl)-3-cyanopyrrole (a) Preparation of
3-carbomethoxy-4-(2,3-dichlorophenyl)pyrrole 10.7 g of 2,3-dichlorophenacylamine hydrochloride and 6 g of methyl 3-dimethylaminoacrylate are heated for 2 hours under reflux in 120 ml of ethanol. Then a solution of 4 g of sodium ethylate in 40 ml of ethanol is added dropwise and the reaction mixture is heated for another hour under reflux. The reaction mixture is then concentrated by evaporation and the oily residue is purified by column chromatography (silica gel; elution with a 3:1 mixture of toluene/ethyl acetate. Melting point: 205°–206° C.

(b) Preparation of the precursor:
4-(2,3-dichlorophenyl)pyrrole-3-carboxylic acid 3.2 g of the 3-carbomethoxy-4-(2,3-dichlorophenyl)-pyrrole obtained in (a) and 40 ml of a 1:1 mixture of methanol and 5N HCl are stirred for hours at 70° C. After it has coled to room temperature, the reaction mixture is poured onto ice and extracted with ethyl acetate. The ester phase is in turn extracted with 10% sodium hydroxide solution. The aqueous extract is washed twice with ethyl acetate, acidified with hydrochloric acid and extracted with ethyl acetate. The organic phase is washed with water, dried over magnesium sulfate and filtered. The filtrate is concentrated by evaporation and the resultant 4-(2,3-dichlorphenyl)pyrrole-3-carboxylic acid melts at 180°–182° C.

(c) Preparation of the final product:
4-(2,3-dichlorophenyl)-3-cyanopyrrole 2.1 g of the free 4-(2,3-dichlorophenyl)pyrrole-3-carboxylic acid obtained in (b) are dissolved in 30 ml of ethanol. The solution is made alkaline with concentrated ammonia and then evaporated to dryness. The residue is dissolved in 50 ml of ethanol. $NH_3$ gas is added (20 atm) to this solution at room temperature in an autoclave and the reaction mixture is kept for 15 hours at 220° C. The reaction mixture, which has cooled to room temperature, is poured into ice/HCl, the precipitate is isolated by filtration and dried at 60° C. The resultant powder is heated with 17 g of polyphosphoric acid in an open vessel at 180° C., the hot mixture is dropped onto ice, made alkaline with NaOH and extracted with ethyl acetate. The combined extracts are concentrated by evaporation and the residue is purified by column chromatography (silica gel; elution with a 4:1 mixture of toluene/ethyl acetate), affording 4-(2,3-dichlorophenyl)-3-cyanopyrrole of m.p. 148°–150° C.

Example P8

Preparation of

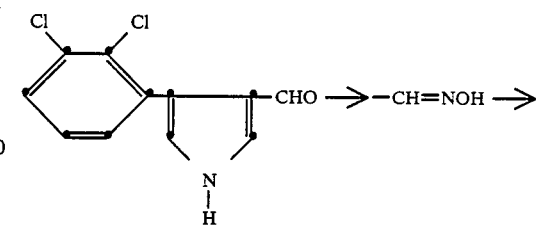

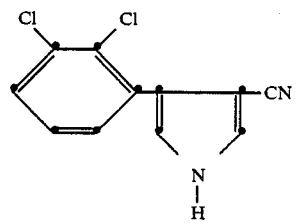

4-(2,3-dichlorophenyl)-3-cyanopyrrole (a) Preparation of
3-formyl-4-(2,3-dichlorophenyl)pyrrole 5.4 g of 3-dimethylaminoacrolein, 3.2 g of 2,3-dichlorophenacylamine hydrochloride and 60 ml of ethanol are heated for 1½ hours under reflux. Then a solution of sodium ethylate in ethanol (prepared from 1 g of sodium and 15 ml of ethanol) is added dropwise and the reaction mixture is heated under reflux for another 30 minutes. After it has cooled to room temperature, the reaction mixture is poured into ice/water and neutralised with hydrochloric acid. The precipitate is washed with water, dried in vacuo, and the dry residue is purified by column chromatography (silica gel; elution with a 4:1 mixture of toluene/ethyl acetate). M.p. 152°–154° C. IR (solid/KBr) in $cm^{-1}$: 1655 (CO). $^1$H-NMR ($CDCL_3$) in ppm: 7.0 (broad s, 1H); 7.3 (m, 2H); 9.66 (s, 1H); 11,9 (s, 1H, H replaceable with $D_2O$). Mass peak at 204. This substance is novel, has fungicidal activity, and falls within the ambit of the invention.

(b) Preparation of
hydroxyiminomethyl-4-(2,3-dichlorophenyl)pyrrole 5.0 g of the 3-formyl-4-(2,3-dichloropheny)pyrrole obtained in (a), 1.7 g of hydroxylamine hydrochloride and 2.4 g of sodium acetate are stirred for 3 hours at 80° C. in 80 ml of ethanol. After it has cooled to room temperature, the reaction mixture is poured onto ice and stirred for 30 minutes. The precipitate is isolated by filtration, washed with water and dried, affording 5.02 g of 3-hydroxyiminomethyl-4-(2,3-dichlorophenyl)pyrrole as syn/anti mixture of m.p. 158°–160° C. This substance is also novel, has fungicial activity and falls within the ambit of the invention.

(c) Preparation of the final product:
4-(2,3-dichlorophenyl)-3-cyanopyrrole 3.2 g of the 3-hydroxyiminomethyl-4-(2,3-dichlorophenyl)pyrrole obtained in (b) are kept for 5 hours at c. 100° C. in 50 ml of acetic anhydride, then cooled to room temperature, poured into ice/NaOH, and the resultant mixture is stirred for 2 hours. The precipitate is dissolved in ethyl acetate, washed with water, and the ester phase is dried over magnesium sulfate. The residue is purifed by column chromatography (silica gel; elution with a 4:1 mixture of toluene/ethyl acetate). Melting point: 149°-151° C.

The compounds of formula I listed in Table 4 are also prepared by methods corresponding to those described above.

TABLE 4

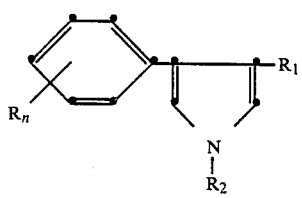

| Compound | $R_n$ | $R_1$ | $R_2$ | m.p. [°C.] |
|---|---|---|---|---|
| 4.1 | H | CN | H | 120–123 |
| 4.2 | 3-Cl | CN | H | 138–140 |
| 4.3 | 2,4-Cl$_2$ | CN | H | 150–152 |
| 4.4 | 4-Cl | CN | H | 153–155 |
| 4.5 | 4-F | CN | H | 137–139 |
| 4.6 | 3-CH$_3$ | CN | H | 109–111 |
| 4.7 | 3-F | CN | H | 138–139 |
| 4.8 | 3-Br | CN | H | 132–134 |
| 4.9 | 3-CF$_3$ | CN | H | 87–89 |
| 4.10 | 2-Cl | CN | H | 136–138 |
| 4.11 | 2,3-Cl$_2$ | CN | H | 152–154 |
| 4.12 | 2,5-Cl$_2$ | CN | H | 137–142 |
| 4.13 | 2-Br | CN | H | 135–138 |
| 4.14 | 2,3-Cl$_2$ | COOCH$_3$ | H | 205–206 |
| 4.15 | 2,3-Cl$_2$ | CHO | H | 152–154 |
| 4.16 | 3-Cl | COOCH$_3$ | H | 187–189 |
| 4.17 | 3,4-Cl$_2$ | COOCH$_3$ | H | 183–186 |
| 4.18 | 2-Cl | COOCH$_3$ | H | 198–200 |
| 4.19 | 2,3-Cl$_2$ | COOC$_3$H$_7$—i | H | 153–156 |
| 4.20 | 2,3-Cl$_2$ | COOC$_2$H$_5$ | H | 149–151 |
| 4.21 | 2,3-Cl$_2$ | CN | CH$_2$CH$_2$CN | |
| 4.22 | 2,3-Cl$_2$ | CN | CH$_2$CH$_2$COOCH$_3$ | |

The described process, including all partial steps, constitutes an object of this invention.

What is claimed is:

1. A process for the preparation of a 4-phenylpyrrole derivative of the formula I

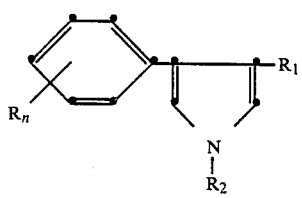

wherein
R$_1$ is CN,
R$_2$ is hydrogen,
R is halogen, C$_{1-6}$alkyl or C$_1$–C$_6$haloalkyl, and n is 0, 1 or 2,
which comprises reacting a phenacylamine of formula II

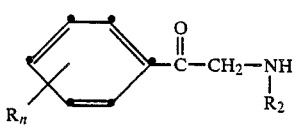

in the form of an acid addition salt of a hydrohalic acid, sulfuric acid or a sulfonic acid, in an inert solvent or mixture of solvents, in the temperature range from 0° to +120° C., with a compound of formula III

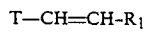

T—CH=CH-R$_1$ (III)

to give an intermediate of formula IV

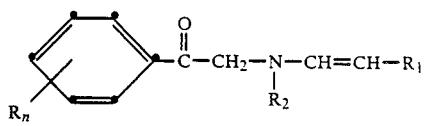

and cyclizing said compound of formula IV, at a temperature of 0° to +120° C., in an inert solvent or mixture of solvents, in the presence of an oxide, hydride, hydroxide, carbonate, carboxylic acid salt or alcoholate of an alkaline earth metal or of an alkali metal, a trialkylamine or a pyridine as base, to give a compound of formula I, in which formulae II, III and IV above, the substituents R$_1$, R$_2$ and R$_n$ are as defined for formula I, T is a group selected from —OZ, —N(R$_3$)(R$_4$), —OCOR$_a$, —OSO$_2$R$_b$ or —SR$_c$,
where
Z is C$_1$–C$_6$alkyl, phenyl or phenyl which is substituted in the para-position by halogen or C$_1$–C$_3$alkyl, an alkali metal atom or an alkali earth metal atom, each of
R$_a$ and R$_b$ independently of the other is C$_1$–C$_6$alkyl, or phenyl which is unsubstituted or substituted by halogen or C$_1$–C$_3$alkyl,
R$_c$ is C$_1$–C$_3$alkyl, C$_1$–C$_3$haloalkyl or phenyl which is unsubstituted or substituted by halogen or C$_1$–C$_3$alkyl,
and each of
R$_3$ and R$_4$ independently of the other is C$_1$–C$_6$alkyl or, together with the amine nitrogen atom, they form a pyrrolidine, piperazine, perhydrothiazine, morpholine, piperazine, oxazolidine, thiazolidine, imidazolidine or pyrazoline ring.

2. A process according to claim 1, which comprises cyclising the phenacylamine of formula II, in the form of an acid addition salt, with a compound of formula II, in the presence of a base, direct to a 4-phenylpyrrole derivative of formula I.

3. A process according to claim 1, which comprises first isolating and then cyclising the compound of formula IV, in the presence of a base, to a 4-phenylpyrrole derivative of formula I.

4. A process according to claim 1, which comprises using a starting material of formula II, wherein R is halogen and n is 1 or 2.

5. A process according to claim 4, which comprises using a starting material of formula II, wherein R is fluorine, chlorine or bromine and n is 2.

6. A process according to claim 5, which comprises using a starting material of formula II, wherein R$_n$ is 2,3-dichloro.

7. A process according to claim 1, which comprises reacting 2,3-dichlorophenacylamine in the form of a hydrohalic acid addition salt, in the temperature range from 0° to 120° C. and in the presence of an inert solvent, with a compound of formula III, wherein R$_1$ is CN and T is a group selected from —N(CH$_3$)$_2$,

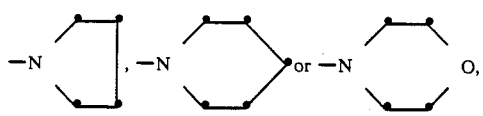

—OK or —ONa, to give 3-(2,3-dichlorophenacylamino-acrylonitrile, and cyclizing this compound, in the presence of a base, to give 4-(2,3-dichlorophenyl)-3-cyanopyrrole.

8. A process according to claim 1, wherein the solvent by itself or as component of a solvent mixture is an aliphatic or aromatic hydrocarbon, an ether, a nitrile, an N,N-dialkylated amide, dimethylsulfoxide, a ketone, an alcohol or water.

9. A process according to claim 1, wherein the phenacylamine of formula II is employed in the form of the hydrochloride or hydrobromide acid addition salt.

10. A process according to claim 1, wherein the reaction is carried out in the temperature range from +30° to +80° C.

11. A process according to claim 1, which comprises using a compound of formula III, wherein T is a group selected from —N(CH$_3$)$_2$, —N(C$_2$H$_5$)$_2$,

—OK or —ONa

12. A process according to claim 11, wherein T is —N(CH$_3$)$_2$ or —N(C$_2$H$_5$)$_2$.

13. A process according to claim 1, which comprises reacting 2,3-dichlorophenacylamine in the form of a hydrohalic acid addition salt, in the temperature range from 0° to 120° C. and in the presence of an inert solvent, with a compound of formula III, wherein R$_1$ is CN and T is a group selected from —N(CH$_3$)$_2$, —OK or —ONa, to give 3-(2,3-dichlorophenacylamino-acrylonitrile, and cyclising this compound, in the presence of a base, to give 4-(2,3-dichlorophenyl)-3-cyanopyrrole.

14. A process according to claim 1, wherein the reactants are employed in equimolar amounts.

* * * * *